Nov. 17, 1953 C. WESCHCKE Plant Pat. 1,229

BLACK WALNUT TREE

Filed Sept. 13, 1951

INVENTOR.

Carl Weschcke

Patented Nov. 17, 1953

Plant Pat. 1,229

UNITED STATES PATENT OFFICE 1,229

BLACK WALNUT TREE

Carl Weschcke, St. Paul, Minn.

Application September 18, 1951, Serial No. 247,133

1 Claim. (Cl. 47—62)

The present invention relates to a new and distinct variety of ornamental, edible and hardy black walnut tree (botanical classification, *Juglans nigra*), originating as a seedling of the Minnesota black walnut grown in applicant's breeding plot near River Falls, Wisconsin, of which the following is a specification, reference being had to the accompanying drawing, forming part thereof.

A substantial number of seed of the Minnesota black walnut was planted in such plot during 1920 and the trees produced by such seed have been made the subject of careful and continued inspection together with selection with respect to desirable characteristics. The parent tree of the instant variety, which originated as one of these seedlings, fruited and was observed to be of novel character.

The variety herein disclosed, characterized by its thin-shell and two-lobe structure, has a full-meated kernel of mild and pleasing taste, the flavor of which is unlike the strong, black walnut flavor but more like that of a butternut, the nut meat thereof being very tender. The nut is elongated in shape; a transverse cross-section shows a rectangular shape, the nut being pointed at both ends, the basal end being sharper than the apex. A distinguishing feature of the basal end is that it is conical, the base of the cone being recessed into the body of the shell, the apex being a much more blunt cone, not recessed but smoothly connecting into the shell.

In its growth habit, the new variety tree is very hardy, the seed having originated in Minnesota, and it lends itself readily by graftage on its own species. On February 16, 1936, it withstood a minimum temperature of 47° below zero Fahrenheit, without damage.

This new variety has been asexually reproduced by grafting and budding in Pierce County, Wisconsin, and comes into bearing 3 to 5 years after graftage.

Figure 1:
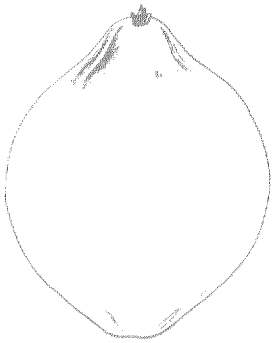
Figure 1 is a full scale drawing of dried walnut in hull, natural size, and indicates the general size and shape.
Figure 2:
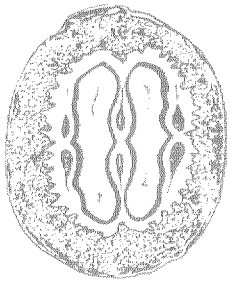
Figure 2 is a vertical view of transverse section thru center of nut including the hull, shell and kernel, which shows the proportion of kernel section to that of shell and hull, indicating the plump nature of the kernel.
Figure 3:
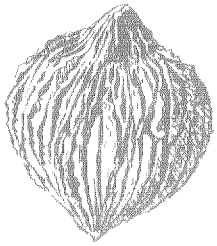
Figure 3 is a view of the nut in the same position, but with hull removed to indicate its general shape and contour after hulling.
Figure 4:
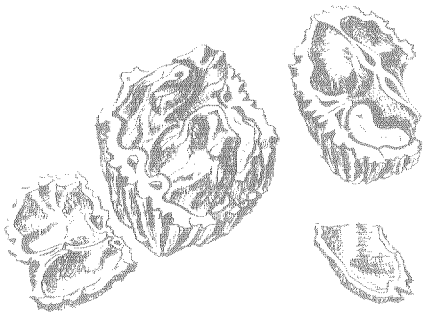
Figure 4 is a vertical view of cracked nut, showing released kernel and the shallow convolution of inside structure of the shell case.

Asexual reproduction of this new variety shows the foregoing characteristics come true to form and are established.

The specimen described was grown at River Falls, Wisconsin.

The following is a detailed description of the new variety:

Seedling: Seed parent—Mixed seed from wild black walnut trees from Minnesota.

Maturity season: October 15 and later, depending on season and location, in Pierce County, Wisconsin. Nuts can be readily hulled clean after drying, which requires several weeks, if dried in open, or can be hulled green and washed leaving the shell light colored and presenting a more marketable appearance.

Tree: Large, vigorous, hardy.

*Productivity.*—Parent tree growing in very poor shallow soil which produces a stunted tree and small but regular crops of nuts. When grafted on stocks growing in much better soil the results indicate much better productivity and larger nuts, with the same annual regularity of bearing. In our nursery experience the grafts begin to bear the third season after grafting. No record is available of year-by-year production since the parent tree is very stunted in growth and grafted trees are still too small to contribute reasonable sized crops for comparative record. Based on the experience with known varieties, such as the Thomas, Ohio, Paterson, Rohwer, and Ten Eyck walnuts, all unpatented, this instant variety compares favorably and similar productivity can be expected under growth conditions analogous to the other mentioned varieties of black walnut, according to experience here at River Falls, Wisconsin.

*Foliage.*—The leaf is pinnately compound, containing from 11 to 15 leaflets. Leaflets have a distinct curve, the curve being greatest on the edge which extends away from the main branch to which the leaflet is attached. The edge closest to the base of the leaf has the flattest curve. The width of this ½ of the leaf measures $^{19}/_{32}$ inches from the central vein to the outer edge whereas the ½ of the leaf away from the base measures $^{12}/_{16}$ from the central vein to the outer edge. This resulting curve gives a more graceful appearance to the whole leaf than the average walnut leaf generally assumes. An average leaf containing 15 leaflets measured 13 inches on July 1, 1953. The largest leaflets on this specimen measured 4 inches from the main stem to the end of the leaf. The underside of the leaf is a lighter, dull-colored green than the outer surface.

Flowers: Pistallate flowers bright red; catkins full and well laden with pollen.

Nuts:

*Ripening.*—Even; time of harvesting October 15 and later.

*Quantity.*—Medium bearer.

*Maturity.*—Earlier than average black walnuts in this locality.

*Tenacity.*—Can be easily shaken down when ripe.

*Cluster.*—Size is medium; average number of nuts 3 to 4.

*Size.*—Length dry in hull—$2\frac{3}{8}$ inch; diameter, dry in hull—$1\frac{3}{4}$ by $1\frac{13}{16}$ inch; length when hulled dry— $1\frac{11}{16}$ inches, diameter is $1\frac{1}{16}$ x $1\frac{5}{16}$ inches.

*Shape.*—Elongated; base-conical, recessed; point-blunt cone.

*Shell.*—Thin; cracks easily and releases by hammer blow causing vertical stress through its greatest latitude; releases kernel in whole quarters and sometimes half kernels. Structure distinctly bilobate with smooth, shallow convolutions of internal parts.

Kernel: Light cream color, very plump and oily. Pellicle smooth, shiny with veins of darker color running radially from center outwardly in curves. General color light brown.

*Flavor.*—Sweet, rich, oily.

*Shape.*—Oval halves—distance through the suture being approximately ½ of the width of the kernel; convolutions shallow and smooth permitting ease of extraction.

*Keeping qualities.*—Dried nuts in the hull stored at room temperatures have kept without deterioration for three years—no rancidity whatever being observed in the normal flavor.

*Texture.*—Friable; oily.

Resistance to:

*Insects.*—Nuts have not been attacked by any insect, including butternut curculio; foliage is subject to walnut leaf caterpillar no more than average black walnuts are.

*Disease.*—No disease has been recorded in over 25 years of observation.

I claim:

A new and distinct variety of walnut tree characterized as to novelty by its hardiness to withstand extremes of temperature, the nuts thereof being at variance with the normal shape and size of the ordinary local black walnut, and having a thinner shell, good flavor, plump kernel, filling shell cavity and removable in halves and quarters; the light color of the pellicle and substance of kernel; and the shallow inner convolutions of the shell permitting easy extraction; keeping qualities being exceptional (3 years or longer at normal room temperature), all of which is substantially shown herein and described.

CARL WESCHCKE.

References Cited in the file of this patent

UNITED STATES PATENTS

| Number | Name | Date |
|---|---|---|
| Pl. Pt. 1,063 | Boellner | Jan. 1, 1952 |
| Pl. Pt. 1,064 | Johnson | Jan. 1, 1952 |